(12) United States Patent
Yung-Ping Chien et al.

(10) Patent No.: US 8,721,860 B2
(45) Date of Patent: May 13, 2014

(54) PROTEIN MULTI-BLOTTING METHOD AND DEVICE

(75) Inventors: Stanley Yung-Ping Chien, Zionsville, IN (US); Hiroki Yokota, Carmal, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 404 days.

(21) Appl. No.: 13/282,030

(22) Filed: Oct. 26, 2011

(65) Prior Publication Data

US 2012/0103811 A1 May 3, 2012

Related U.S. Application Data

(60) Provisional application No. 61/407,253, filed on Oct. 27, 2010.

(51) Int. Cl.
*G01N 27/447* (2006.01)

(52) U.S. Cl.
USPC .......................... 204/464; 204/614

(58) Field of Classification Search
CPC ............................................... G01N 27/44739
USPC .................................. 204/464, 614
See application file for complete search history.

(56) References Cited

U.S. PATENT DOCUMENTS 4,541,910 A * 9/1985 Davis et al. .................. 204/464

OTHER PUBLICATIONS

Lakhotia, S. C. & B. N. Singh, "A simple and inexpensive 'Western blotting' apparatus", Indian Journal of Experimental Biology, vol. 31, Mar. 1993, p. 301-302.*

* cited by examiner

*Primary Examiner* — J. Christopher Ball
(74) *Attorney, Agent, or Firm* — C. John Brannon; Brannon Sowers & Cracraft PC (57) ABSTRACT

A technique for producing multiple protein blots from a single gel, including entering the number 'n' membranes to be blotted into microprocessor memory, determining calibration constants for a gel batch, inputting calibration constants into microprocessor memory, and calculating 'n' voltage/time profiles for simultaneous blotting. A gel layer from the gel batch is treated with a protein sample, 'n' membranes are placed onto the gel layer to yield a gel pack, and the gel pack is placed between an electrode plate maintained at a fixed first voltage and an array of 'n' spaced generally parallel electrodes. The voltage to each respective 'n' spaced generally parallel electrodes is varied over time according to a respective 'n' voltage/time profile to transfer proteins to each respective 'n' membranes to yield blotted membranes to yield 'n' respective blotted membranes.

11 Claims, 13 Drawing Sheets

Fig. 11

PROTEIN MULTI-BLOTTING METHOD AND DEVICE

CROSS-REFERENCE TO RELATED APPLICATIONS

This patent application claims priority to co-pending U.S. Provisional Patent Application Ser. No. 61/407,253, filed on Oct. 27, 2010.

TECHNICAL FIELD OF THE INVENTION

The invention relates generally to the field of analytical biochemistry and, specifically, to a method and apparatus for simultaneously generating multiple protein blots.

BACKGROUND

The Western blot technique for detecting and identifying specific proteins in biological samples is commonly used among life scientists. This blotting technique utilizes gel electrophoresis to fractionate native or denatured proteins based on their migration speed (mobility) in a gel while under an electrical field. The proteins, trapped and size-fractionated in a gel, are transferred to and immobilized by a positively-charged membrane. (See FIG. 1) Using primary antibodies specific to the target proteins, as well as secondary antibodies for signal amplification and visualization, expression and modification of the target proteins can be investigated. Although the procedure is well-established, and many tools are available for gel fractionation and blotting, one of the bottlenecks is its limited efficiency and controllability during the blotting procedure.

In most applications of Western blotting, there is a need to evaluate expression levels of multiple protein targets. Signal transduction pathways, for instance, are often activated by protein modifications such as glycosylation and phosphorylation. It is important to be able to determine the amount of signaling molecules that are, in many cases, phosphorylated. However, the current blotting technique can generate only a single membrane per gel, and thus life scientists usually have to prepare multiple gels. When the results from multiple gels are compared, one source of error may arise from potential chemical and physical variations among the gels. Furthermore, since the preparation of protein samples, running gels, and transferring to membranes are time consuming and costly, it is desirable to develop a blotting procedure that enables multiple blotting from a single gel. Such a procedure could reduce potential inconsistencies during sample loading, electrophoresis, and blotting, which are affected by varying factors including operational time, temperature, and chemical composition.

Thus, there is a need for a quicker and more efficient protein separation technique. The present novel technology addresses this need.

SUMMARY

The present novel technology relates to protein blotting. One object of the present invention is to provide an improved method and apparatus for generating protein blots. Related objects and advantages of the present invention will be apparent from the following description.

DETAILED DESCRIPTION

For the purposes of promoting an understanding of the principles of the novel technology and presenting its currently understood best mode of operation, reference will now be made to the embodiments illustrated in the drawings and specific language will be used to describe the same. It will nevertheless be understood that no limitation of the scope of the novel technology is thereby intended, with such alterations and further modifications in the illustrated device and such further applications of the principles of the novel technology as illustrated therein being contemplated as would normally occur to one skilled in the art to which the novel technology relates.

Blotting is a common protein transfer technique widely used for molecular analysis in the life sciences. Blotting involves the transfer of electrophoretically separated protein samples, immobilized in a polyacrylamide gel, to a blotting membrane. The present state of the art for the protein transfer is placing a gel, which has a mixture of proteins with various electrophoretic mobilities, in a constant electric field and generating one membrane per gel. When multiple blotting copies are needed as in many applications, multiple gels need to be prepared for each of the proteins to be analyzed. Two blotting copies from a single protein gel, for instance, can be used for identifying a total amount of proteins of interest as well as its specific subpopulation level, such as phosphorylated isoform.

As shown in FIGS. 2-11, the present novel technology relates to a technique 10 of producing multiple membranes 15 from a single gel, regardless of protein sizes. The first advantage of this multi-blotting technique 10 is that a user can produce multiple membranes 15 of identical protein samples. The ability of producing identical membranes 15 is useful, particularly in a comparative study, and also eliminates one source of error arising from chemical and physical differences. The second advantage of this method 10 is that it significantly reduces labor and chemical costs.

In order to uniformly transfer proteins regardless of their sizes, the novel technology includes 1 the introduction of a new multi anode array 20 (or multi cathode array 21) design for the application of varying voltages to different proteins during blotting, 2 a method 30 to determine different voltage levels to be applied to the multi anode array 20 (or multi cathode array 21), and 3 a method 40 to use pulse width modulated (PWM) DC voltages to provide different average voltage levels to the multi anode (or multi cathode) for blotting.

The multi anode array 20 enables the application of varying voltages to proteins of different sizes (i.e., mobilities). The mobility of any protein can be approximated to be proportional to the transfer voltage and exposure time. Introducing multiple anodes 45 allows the application of different respective voltages 50 and/or respective field exposure durations 55 for proteins of different mobility during blotting.

Typically, protein mobility is characterized by a previous step of protein fractionation 60 using electrophoresis in a vertical gel. In this vertical gel, proteins under the constant voltage move in the same direction with varying mobility (see FIG. 2). Generally, smaller proteins have higher mobility in a given gel.

Description of Multi Anodes Plate

Figure 2:
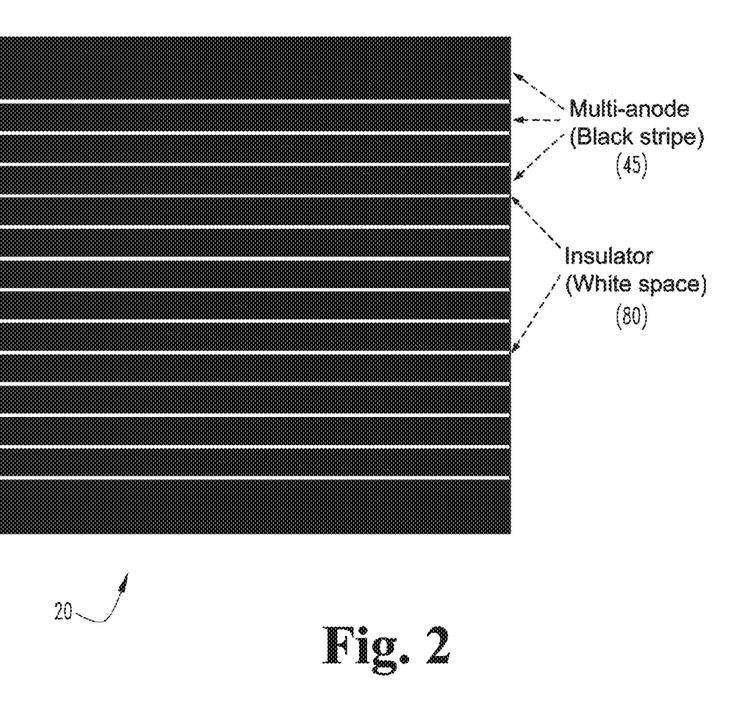
FIG. 2. Schematic view of a multiple anode array according to a first embodiment of the present novel technology.
Figure 3A:
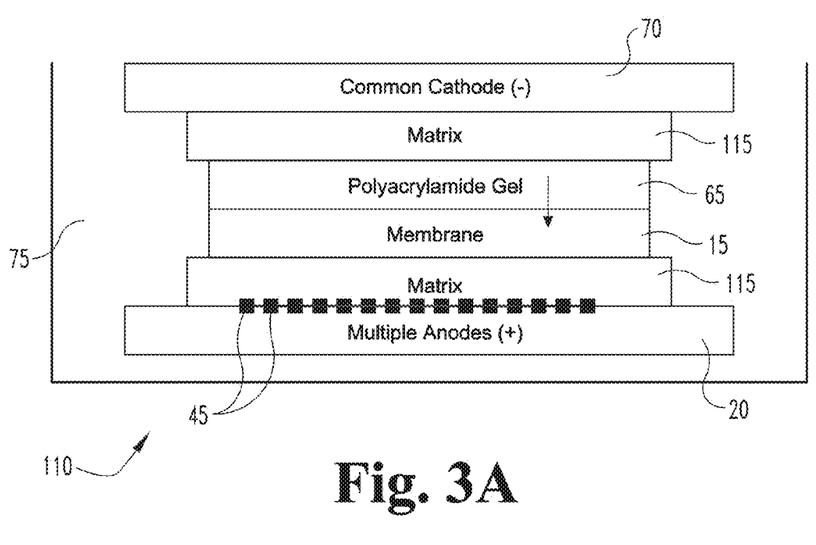
FIG. 3A. Schematic view of a first embodiment blotting apparatus according to a first embodiment of the present novel technology incorporating the multiple anode array of FIG. 2.
Figure 3B:
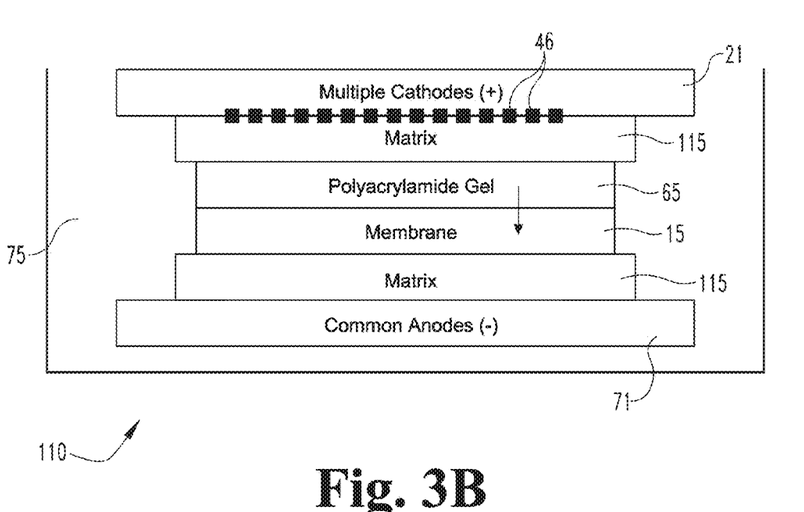
FIG. 3B. Schematic view of an alternate embodiment blotting apparatus according to a second embodiment of the present novel technology incorporating a multiple cathode array.
Figure 4A:
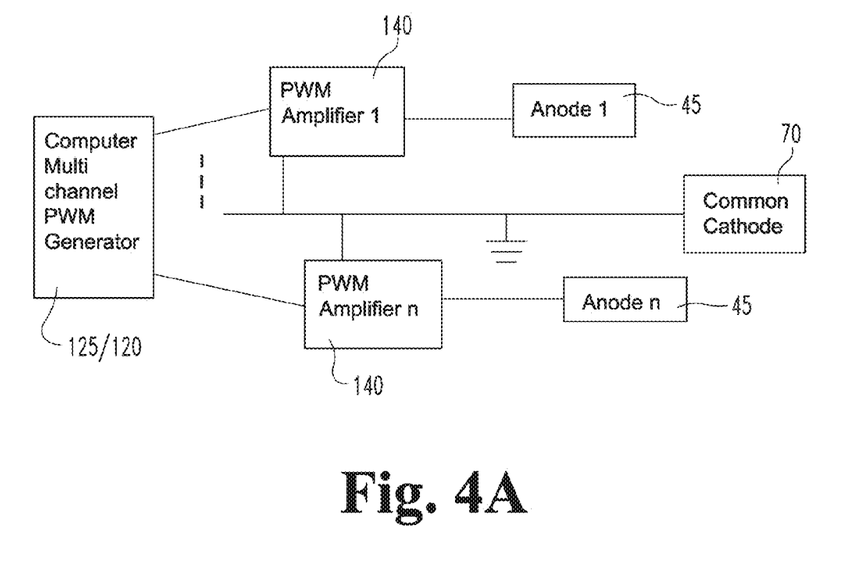
FIG. 4A. Schematic view of the embodiment of FIG. 3A as connected to a microprocessor and power source.
Figure 4B:
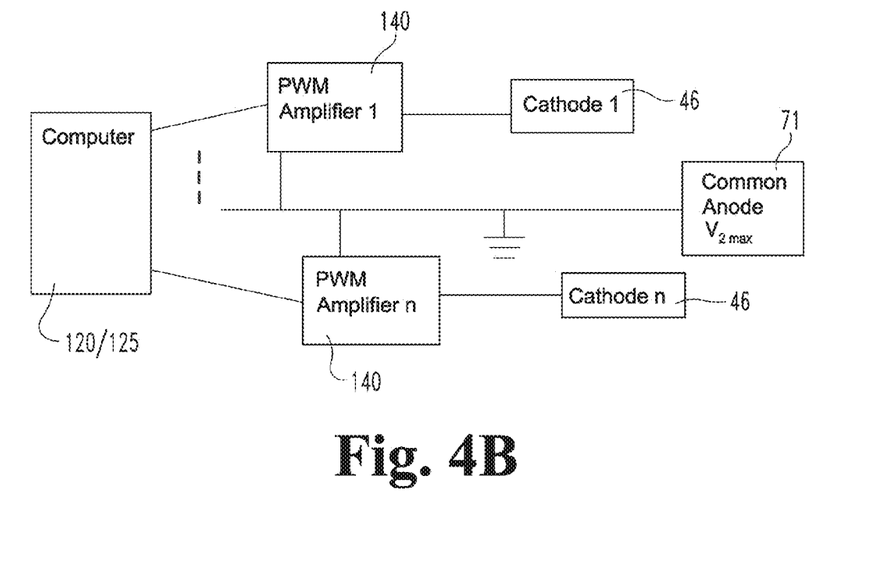
FIG. 4B. Schematic view of the embodiment of FIG. 3B as connected to a microprocessor and power source.

To generate multi blotting membranes 15 from a single gel 65, an array 20 of multiple independent anodes 45 is positioned opposite a common cathode 20, enabling the application of different voltage 50 and/or running time 55 for proteins of different sizes. The multi anode array 20 is arranged on a non-conductive plate 75, as shown in FIG. 2. Each anode 45 is represented by a black stripe, and the insulated gap 80 between two adjacent anodes 45 by a white stripe. There is no theoretical limitation on the number of anodes 45 or the width of an anode 45, but for generating a practical voltage profile the width of each anode 45 might typically be about 4 mm and the gap width 1 mm. Using a standard blotting protocol, a gel 65 and a blotting membrane 15 are configured as shown in FIG. 3A and FIG. 3B. A higher voltage is typically applied to the anode 45 that is in electric communication with a group of larger proteins.

In order to apply well-controlled voltages to proteins in the gel 45, protein mobility 85 is typically evaluated during size fractionation 60 using electrophoresis in a vertical gel 90. This mobility 85 is affected by various factors 95 besides protein sizes 95A, including gel composition 95B and properties 95C, buffer solution 95D, electrophoretic voltage 95E, running time 95F, and the like. Electrophoretic voltage 95E and running time 95F are recorded and used for determining an appropriate voltage profile 100 for blotting. Likewise, gel and buffer solution factors 105, 95B, 95C, 95D, are taken into account if they are going to differ between the fractionation pre-step system and the blotting system 110.

One example theoretical basis for determining a non-uniform voltage profile for 106 multi-membrane blotting 10 for proteins with varying mobility follows. For a protein P migrating in vertical electrophoresis, when the time (t) is constant, the protein-moving distance (d) is proportional to the voltage; when the voltage is constant, the protein moving distance (d) is likewise proportional to the time (t). Therefore, the protein moving distance in vertical electrophoresis can be described by equation 1:

$$d = kvt \qquad (1)$$

where k is a coefficient constant, v is the voltage and t is time for blotting.

The constant k is determined by three factors, the properties of the gel 65, the protein sizes, and the electrical conductivity of the buffer solution 95D. Equation (1) also may be applied in the horizontal blotting. In both vertical and horizontal systems 105, 110, the buffer solution 95D and the presence or absence of supporting matrices 115 and blotting membranes 15 may be different. Let the constant k for horizontal transfer be $k_h$ and the constant k for vertical electrophoresis be $k_v$, the ratio of $a=k_v/k_h$ is related to electrical conductivities of the electrophoresis system and is approximated to be a constant for all proteins. In common protein experiments, there are a small number of buffer solutions 95D. Therefore, the constant a is readily determined.

Protein vertical migration may be modeled with $d_1 = r*L$ at a given $v_1$ and $t_1$, where $d_1$ is the migration distance and L is the maximum vertical travel length in the gel and r is a value between 0 and 100%.

If a protein moves a vertical distance $d_1$ in a blotting condition of $v_1$ and $t_1$ and the same protein moves a horizontal distance $d_2$ in a condition of $v_2$ and $t_2$, according to equation 1, the following relationship is valid:

$$d_1 : d_2 = (k_v * v_1 * t_1) : (k_h * v_2 * t_2)$$

$$\Rightarrow (r*L) : d_2 = (k_1 * v_1 * t_1) : (k_2 * v_2 * t_2)$$

$$\Rightarrow k_v * v_1 * t_1 * d_2 = k_h * v_2 * t_2 * r * L$$

$$\Rightarrow v_2 * t_2 = (k_v * v_1 * t_1 * d_2)(k_h * r * L)$$

$$\Rightarrow v_2 * t_2 = (a * v_1 * t_1 * d_2)/(r*L) \qquad 2$$

Note that $v_1$, $t_1$ can be measured in vertical electrophoresis, L is the length of the gel, and $d_2$ is the thickness of the gel. Note also that in this case, $k_1$ and $k_2$ are equivalent to $k_v$ and $k_h$, respectively. The constant a can be predetermined experimentally. The equation 2 is valid for proteins of all sizes across the gel 65 and independent of gel types and protein types. There are two ways to use equation 2 to calculate the voltage and time applied to each anode in horizontal blotting.
1. Regulate running time and constant voltage 55.
2. Regulate transfer voltage with constant running time 50.
   By placing the maximum $v_2$ at a location $r_1*L$, where $r_1$ is close to 0 (e.g., for $r_1=0.1$), $t_2$ can be determined:

$$t_2 = (a*v_1*t_1*d_2)/(r*L*v_2) = (v_1*t_1*d_2)/r*L*v_{2Max}) \qquad 3$$

After $t_2$ is determined, voltage v, at various points (r*L) for r from 0.1 to 1, can be determined:

$$v_2 = (a*v_1*t_1*d_2)/(r*L*t_2) \qquad 4$$
$$= (a*v_1*t_1*d_2)/(r*L*[(v_1*t_1*d_2)/(r_1*L*v_{2Max})])$$
$$= v_{2Max}*a*(r_1/r)$$

$$v_2 = v_{2Max}*a*(r_1/r)$$

Equations 2 and 4 provide the following information:
a. $v_2$ decreases inversely proportional to r for $0.1<r<1$.
b. Proteins of any size may move the same distance $d_2$ in time $t_2$, and $t_2$ can be calculated based on equation 3.

For practical purpose $v_{2Max}$ can be assigned at the location of $L*0.1$ ($r_1=r=0.1$).

Generating Voltages and Time for Multi-Anodes Arrays

Figure 5:
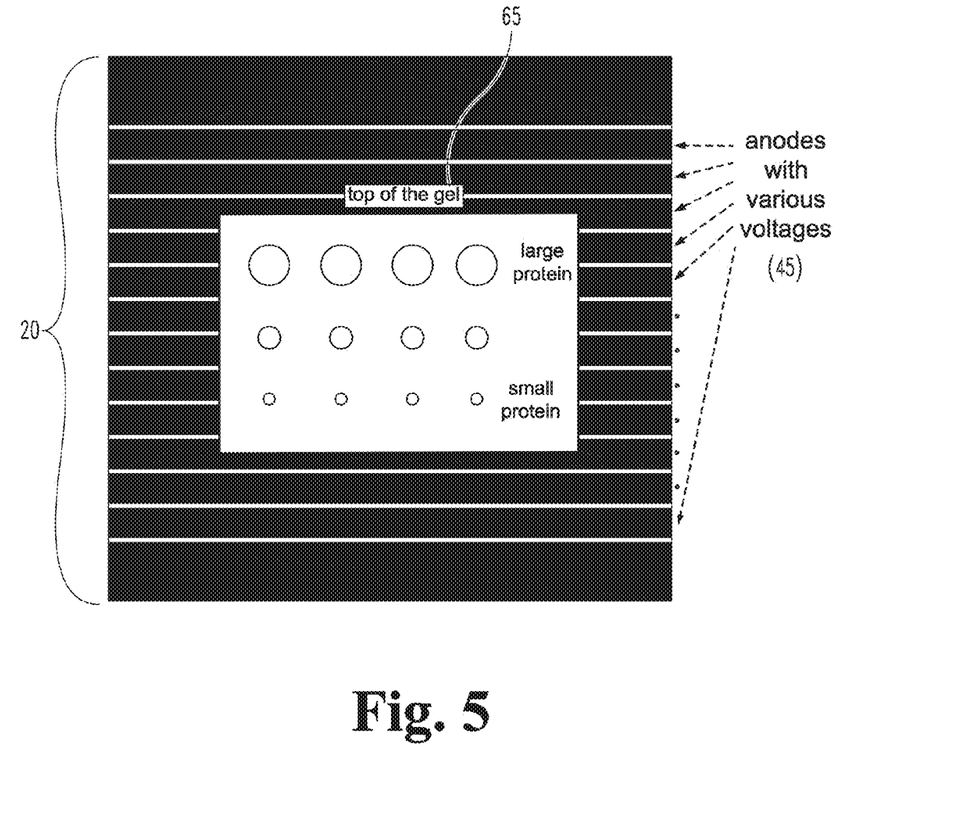
FIG. 5. Schematic view of FIG. 2 superimposed with a diagrammatic view of protein separation.
Figure 6:
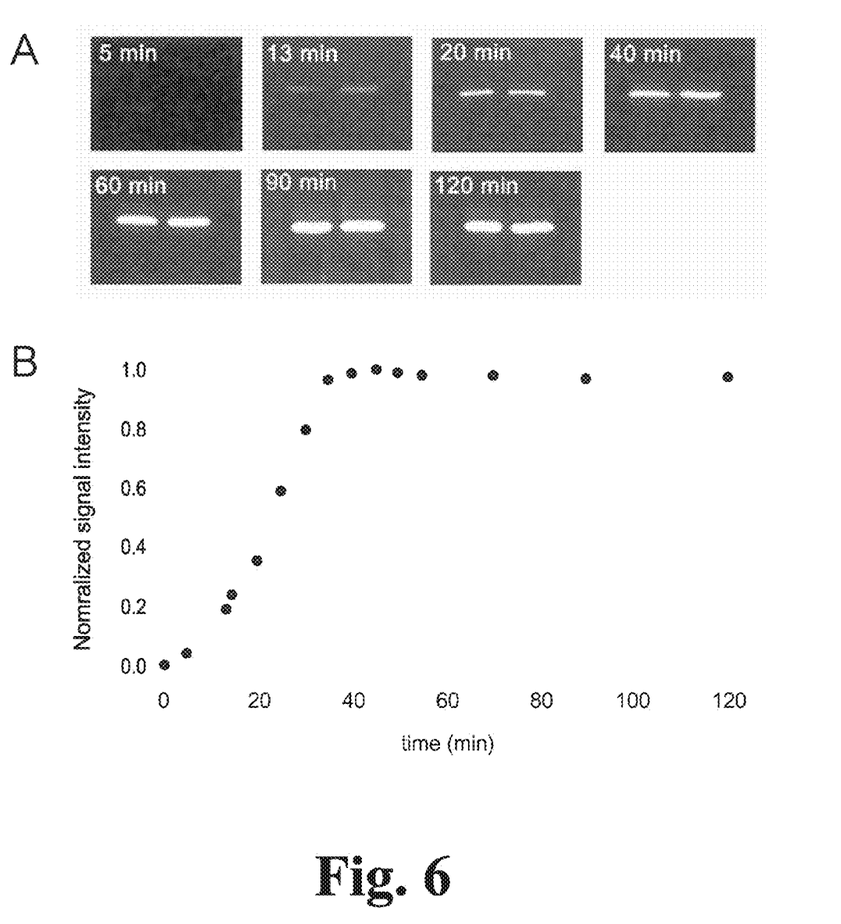
FIG. 6A. Graph of signal intensities of β-actin with various blotting durations, representative blotting images after semi-dry transferring for 5, 13, 20, 40, 60, 90, 120 min.
FIG. 6B. Graph of normalized signal intensities as a function of 15 blotting durations, with maximum intensity set to 1.
Figure 7:
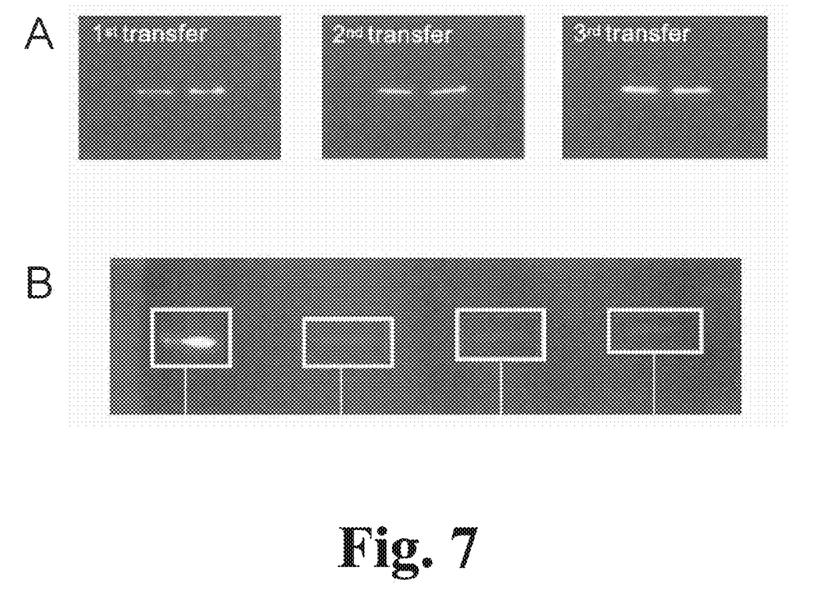
FIG. 7A. Graph of multiple transfers using a non-uniform voltage profile, blotting images of three transfers, transfer time 14.5 min ($1^{st}$ transfer), 6.5 min ($2^{nd}$ transfer), and 15 min ($3^{rd}$ transfer).
FIG. 7B. Graph of differential transfer efficiency using a non-uniform voltage profile, white boxes indicate the expected positions of β-actin bands, in which the right box corresponds to ~15 V, while the left ~2 V does not show any visible band.

Typically, it is undesirable to employ multiple DC voltage sources to generate the well-controlled voltage profile 100 during blotting, since a multiple source approach is not cost effective. Instead, it is more typical to use a single DC voltage source 120 operationally connected to a computer 125, which generates multiple pulse width modulated (PWM) DC voltages 130 and produces the voltage signals 135 for each arrayed anode 45. Each PWM voltage driving signal 135 is typically individually amplified, and all PWM signals 135 are typically amplified with the same gain. The duty cycle of each PWM 135 is determined to make the average PWM voltage 130 after amplification identical to the driving voltage 135. The system block diagram is shown in FIG. 5.

If the amplifier gain is G, the peak voltage of all PWM after amplification is V, and the desired voltage 130 for the anode 45 is calculated based on equation 2 is $v_1$. Then, the duty cycle of the voltage applied to anode I is:

$$\text{PWM Duty cycle for Anode } I = [v_1/(V/G)]*100\% \qquad (5)$$

The frequency of the PWM 130 may be in a wide range from KHz to a minimum 1/t Hz, where t is the time used in size fractionation using the vertical gel 90. When the period of the PWM is set to 1/t Hz, the outcome is equivalent to the case in which a constant voltage is applied with varying time to individual anodes 45.

Operational Procedure

A typical experimental procedure (see FIGS. 10 and 11) using the set-up, illustrated in FIG. 3B, is:
1. Size-fractionate proteins in electrophoresis with a vertical gel apparatus 105.
2. Specify the vertical gel 90 running conditions (e.g., 150 V for 40 min with gel 1 mm thick, and constant a) as well a number of blotting membranes 15 to be made. The microcontroller 125 determines and generates the transfer conditions 100 (e.g., 3-30 V gradients for 10 min).
3. Place the gel 65 to a semi-dry transfer system.
4. Mount a blotting membrane 15 on the top of the gel 65.
5. Conduct the transfer to the mounted membrane 15; transfer conditions 100 are automatically set in step 2.
6. After completing the transfer process 15 for the mounted membrane 15, remove the membrane 15; mount a new membrane 15, and conduct the transfer.
7. Repeat steps 4 to 6 for the number of blotting membranes 15 entered in step 2.

Variations

The method described in section 2 can be achieved using multiple cathodes 46 with a common anode 71.

The Description of Multi Cathodes Plate

In this method, multiple cathodes 46 are placed on a non-conductive plate 75 as shown in FIG. 3A, 3B. There is no theoretical limit on the number of cathodes 46 and the width of each cathode 46. For example, multiple voltages for multiple cathodes 46 can be arranged with the width of each cathode 46 as 4 mm and the gap 80 between two cathodes is 1 mm.

Figure 8:
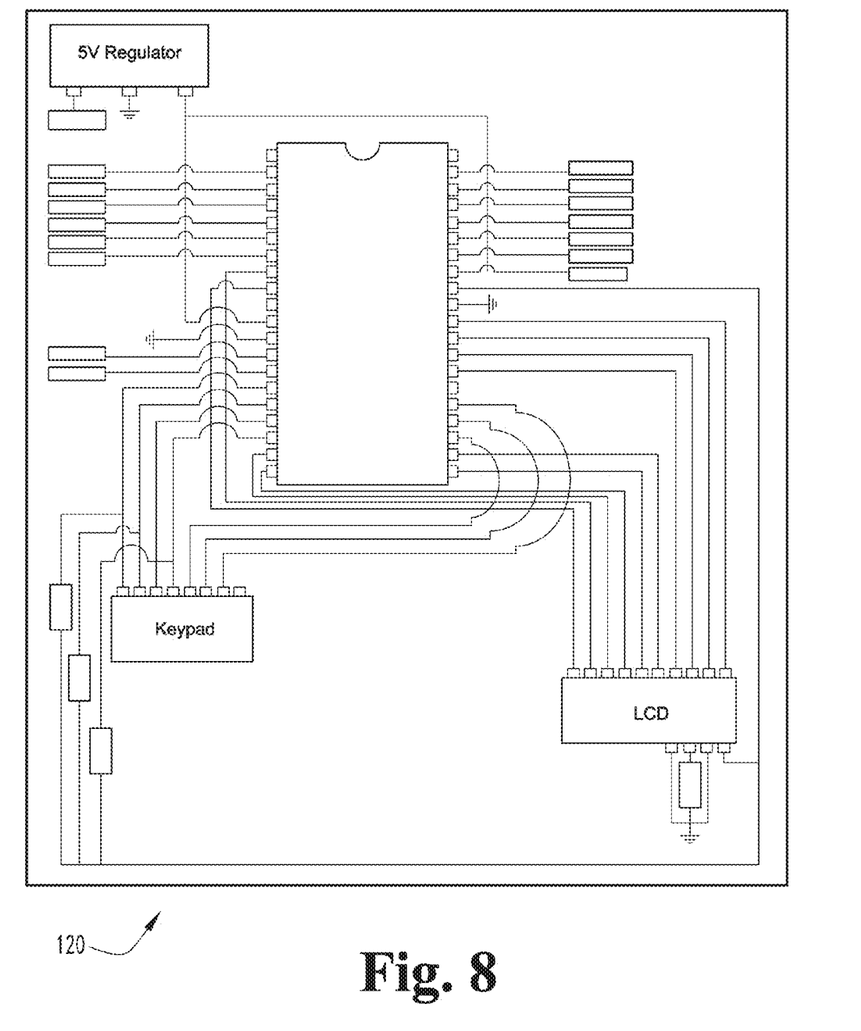
FIG. 8. Schematic diagram of microcontroller circuits for generating a series of PWM signals for establishing a well-controlled voltage profile to an array of anodes, according to the embodiment of FIG. 3A.

The placement of a gel 65 and a membrane 15 in blotting is shown in FIG. 7A and FIG. 7B. The relative orientation of the gel 65 and the multiple anodes array 20 is shown in FIG. 8. Note that the blotting system 110 applies a higher voltage to the anodes 45 where large proteins are transferred.

Generating Voltages and Time for Multi Anodes

Figure 9:
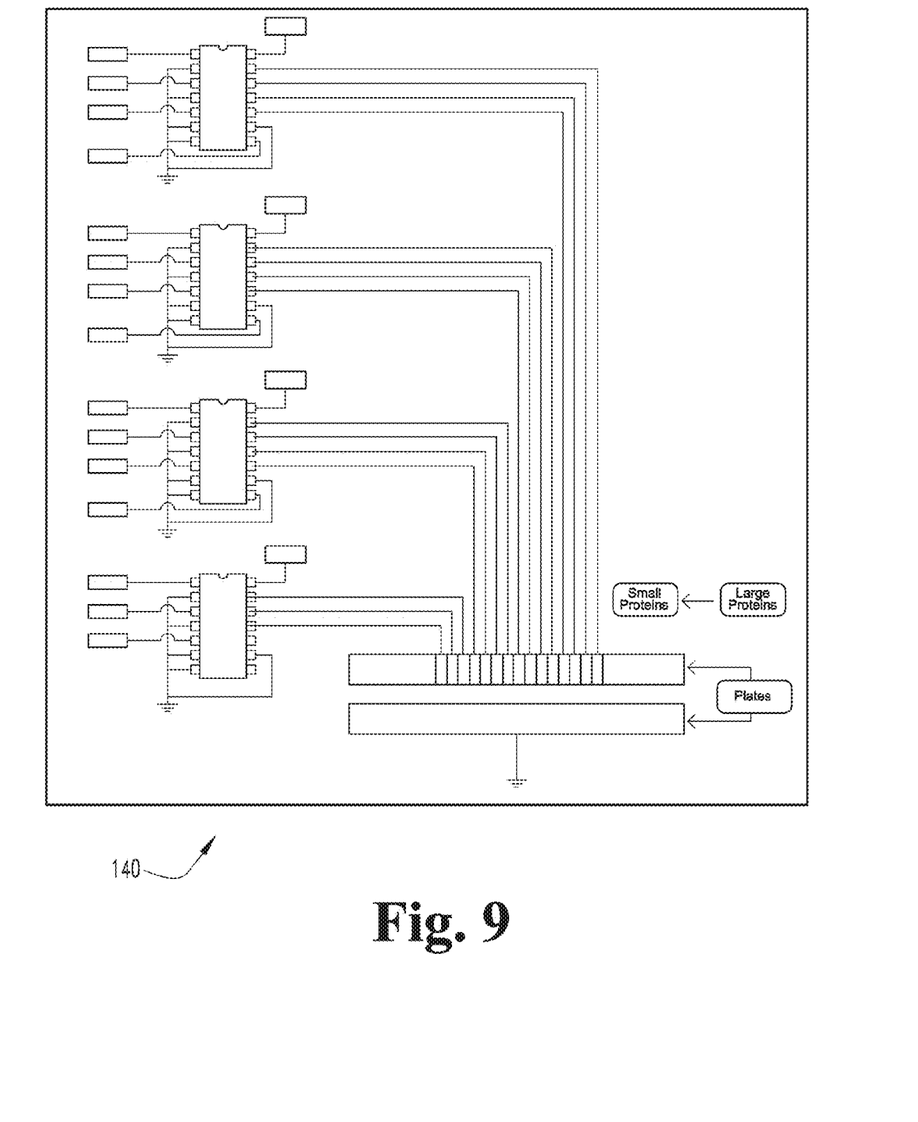
FIG. 9. Schematic diagram of an amplifier circuit for multi-blotting according to the embodiment of FIG. 3A.

This invented method employs a single DC voltage source 120 and a computer 125 for generating multiple pulse width modulated DC voltages 130, and thus a single source 120 produces all voltage signals 135 for all anodes 45. Each PWM driven signal 135 is typically individually amplified, although all PWM signals 135 are amplified with the same gain. The duty cycle of each PWM is determined to make the average PWM voltage 130 substantially identical to the corresponding driving voltage. The system block diagram is shown in FIG. 9.

The amplifier gain is G, the peak voltage of all PWM after amplification is V, and the desired voltage for the anode I calculated based on equation 2 is $v_i$, and the duty cycle of the voltage applied to cathode I becomes:

$$\text{PWM Duty cycle for cathode } I = = [V-v_i]/(V/G)]*100\% \qquad (6)$$

Thus the instant technique is able to:
1. Use multiple anodes 45 and a common cathode 70 (or the inverse 46, 71) for conducting semi-dry blotting and dry blotting.
2. Produce multiple membranes 15 using a single gel 65 that contains proteins of varying sizes.
3. Apply different voltages 100 on the multiple anodes 45 (or multiple cathodes 46) to ensure that proteins of different sizes can be uniformly transferred.
4. Generate different voltages 50, which are applied to the anodes 45, by multiple analog DC voltage sources or pulse width modulated DC voltages 130.
5. Use different running times 55 for applying voltages on the multiple anodes 45 (or multiple cathodes 46) to ensure the proteins of different sizes can be transferred at the same efficiency.
6. Employ PWM to control the voltage 130 for blotting.

In one embodiment, a novel protein blotting device 110 is provided with two functions. First, the blotting system 110 is able to generate multiple (typically three) blotting membranes per gel 65 with equal quality (multi-blotting). Second, proteins with varying sizes (for instance, 20 to 150 kD) are transferred in the same percentage rate in the same blotting procedure without altering transferring time (uniform transferring).

The efficiency of protein transport was investigated by establishing a cumulative signal intensity function P(t), as a function of transferring time, t. For instance, $P(t_1)=\frac{1}{3}$ indicates that one third of proteins transferred for a duration of $t_1$. An electrophoretic voltage profile was derived along the directions of protein migration, in which one third of proteins regardless of their molecular size would be transferred in $t_1$. This voltage profile was applied to a multi-anode plate using a micro-controller based pulse width modulated (PWM) voltage generator (120).

EXAMPLES

Western Blotting

Protein Samples

MC3T3 osteoblast-like cells were cultured in αMEM medium containing 10% fetal bovine serum and antibiotics (50 units/ml of penicillin and 50 µg/ml of streptomycin). Cells were incubated at 37° C. in a humid chamber with 5% $CO_2$ and prepared for experiments at 70-80% confluency. Protein samples were isolated by sonicating cells using a sonic dismembrator and lysed in a protein lysis buffer.

Electrophoresis and Semi-Drying Transferring

Isolated proteins were size-fractionated using 10% SDS gels (1.5 mm thickness). Electrophoresis was conducted using 100 V for 10 min (stacking), followed by 150 V for various durations (separation). Proteins, immobilized in SDS gels, were electro-transferred to Immobilon-P membranes using a semi-dry transferring apparatus. The standard transferring condition was 15 V for 40 min. To evaluate the effects of transferring conditions such as voltages and running times, varying transferring conditions were also examined.

Antibody Reactions and Image Analysis

The Immobolin-P membrane after protein blotting was incubated overnight in a blocking solution (1% milk in a PBS buffer). The membrane was then incubated for 1 hour with monoclonal β-actin antibodies followed by 45 min incubation with goat anti-mouse IgG conjugated horseradish peroxidase. The protein levels were assayed using an ECL Western blotting detection kit, and signal intensities were quantified using a luminescent image analyzer.

Protein Multi-Blotting Device

Prediction of the Blotting Voltage Profile

In order to uniformly transfer proteins regardless of their size in a given transferring time, blotting voltages were regulated for individual proteins. Based on observation in size fractionation, the mobility of proteins was assumed to be proportional to an applied electrophoretic voltage and transferring time. Through experimentation, the blotting voltage profile along the direction of protein migration was observed to achieve a uniform transfer of proteins any size. In the described blotting device, a protein with a normalized mobility of r would receive a local blotting voltage that was inversely proportional to r.

For a protein transferring in a gel, its moving distance, d, can be modeled to be proportional to the electrophorectic voltage, v, and blotting time, t:

$$d = kvt \quad\quad 1$$

with k as a proportional factor. Given that for a fixed time, T, a moving distance is expressed as d=rL, where L=length of the gel, and r=normalized mobility ration between 0 (no mobility) and 1 (maximum mobility). In the described apparatus, any proteins have the same mobility along the thickness of the gel for a constant time with a graded electrophoretic voltage for individual proteins. Assume the largest protein of interest moves $d_{min}$ at $v_{max}$ with $d_{min} = r_{min}L$. Then, v for any protein with a normalized mobility ratio of r can be determined:

$$v = v_{max}(r_{min}/r) \quad\quad 2$$

In summary, the graded electrophoretic voltage in the described apparatus is regulated to be inversely proportional to its normalized mobility rate.

Design of the Multiple Anodes and the Microcontroller Base PWM Generator

Figure 1:
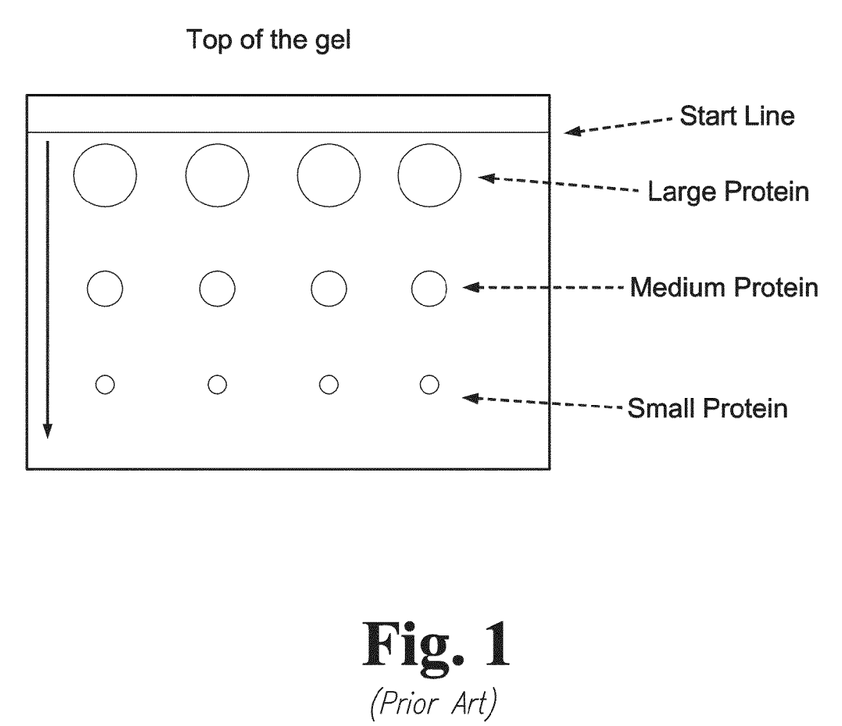
FIG. 1. Schematic view of protein migrating through a gel during electrophoretic size fractionation (prior art).

In one embodiment, the multi-blotting device 110 has a plate with multiple anodes 45 (FIG. 1). With proper regulation of blotting voltage profiles, proteins of the identical molecular size receive the same voltage, while larger proteins are transferred with the higher voltage. Here, a single DC voltage source 120 and a computer-controlled 125 voltage generator provided voltages for all anodes 45 (FIG. 2). This generator provides multiple pulse width modulated (PWM) DC signals 135 of different duty cycles for all anodes 45, in which each PWM signal 135 was individually amplified by a PWM amplifier 140 and applied to one anode 45. The voltage amplification gains are the same to all PWM signals 135. The duty cycle was set to make the average voltage of an amplified PWM equal to the desired driving voltage of the corresponding anode 45. Assuming the amplification gain is G, the peak voltage of all PWM after amplification is V, and the desired voltage for anode I is $v_i$, the duty cycle of the voltage applied to anode I is $[v_i/(V/G)]*100\%$.

Examples

Experimental Evaluation and Validation

Blotting Time and Signal Intensities

Prior to generating multiple blotting membranes 15 from a single gel 65, a relationship of signal intensities to transferring time was built by conducted semi-dry blotting using various transferring times 55. Taking β-actin as an example, representative blotting images 145 are shown for blotting for 5, 13, 20, 40, 60, 90, and 120 min at 15 V (FIG. 6A). The two protein bands in each image 145 were generated using the identical conditions. The signal level after reactions with antibodies was initially increased as the blotting time was lengthened. However, the level was saturated for the transfers for 40 min or longer durations 55. The normalized signal intensities showed that this temporal signal profile was approximated by a cumulative Gaussian distribution function (mean=22 min, and standard deviation=9 min) (FIG. 6B). This cumulative distribution function provided the basis for determining transferring time for each of the multiple blotting membranes 15. Typically, if this cumulative function is a linear function of transferring the same, the same blotting time is applied to all membranes. The Gaussian distribution implies that for generating 3 membranes, the $1^{st}$ and the $3^{rd}$ transferring durations 55 are identical. The $2^{nd}$ transferring duration 55 is calculated 83% of the standard deviation (approximately 7.5 min in our experimental setup).

Multiple Transfers

Based on the relationship between blotting time 55 and signal intensity 50 in the previous experiment, multiple transfers were next conducted (generation of 3 blotting membranes 15) using a single gel 65. Selecting β-actin, the transfer time was chosen to be 15 min ($1^{st}$ transfer), 7 min ($2^{nd}$ transfer), and 15 min ($3^{rd}$ transfer). The result clearly shows that by properly choosing blotting durations 55 it is possible to generate multiple blotting membranes 15, although there are variations in signal intensity among three membranes 15 (FIG. 7A). In each image, two protein bands were processed using the same experimental condition.

Transfer Under a Non-Uniform Voltage Profile

The experiments above support the first design criterion of achieving multiple blotting membranes 15 from a single gel 65. To examine the second design criterion of simultaneously transferring proteins with various sizes, 40 min semi-dry blotting was conducted using a non-uniform voltage profile 100 (FIG. 7B). In this experiment all conditions were identical to the condition employed for generating the results depicted in FIG. 3 except the voltages 50. The voltages 50 applied to four different bands (left to right) were 12.0 V, 3.9 V, 2.3 V, and 1.7 V, respectively. The result using β-actin as an example demonstrates that transfer efficiency is controllable by an applied electrophoretic voltage 100. The left position under 12 V exhibits a clear protein band, but the right position under approximately 1.7 V barely shows a detectable protein band.

Protein Multi-Blotting Device
Design and Prototyping the Multi-Anode Plate

An apparatus 100 was made including microcontroller 125 m connected to multiple anode plate 20, where the width of each anode stripe 45 was set to 4 mm and the width of the gap 80 between two respective anodes 45 was 1 mm. The size of both anode 20 and cathode plates 70 were 18 cm×24 cm, and the device 110 was designed to accommodate gels 65 with size up to 14 cm×17 cm.

Design and Prototyping Multi-Blotting Control Circuits

A PICF184515 microcontroller-based voltage generator 120 was designed and prototyped to provide the designated voltage profile 100 to individual anodes 45 (see FIG. 8). The microcontroller generated PWM voltage signals 135 were amplified. The average voltage of the amplified PWM signal 135 corresponded to the desired voltage for the anode 45.

The maximum voltage of all PWM signals 135, generated by the microcontroller 125, was 5 V with the current of 100 μA. Since the PWM signals 130 did not provide the necessary power for driving a protein transfer, these signals were amplified using a TC 4469 MOSFETS amplifier 140 (see FIG. 9). The maximum voltages of all PWM signals 130 were set to 15 V.

Figure 10:
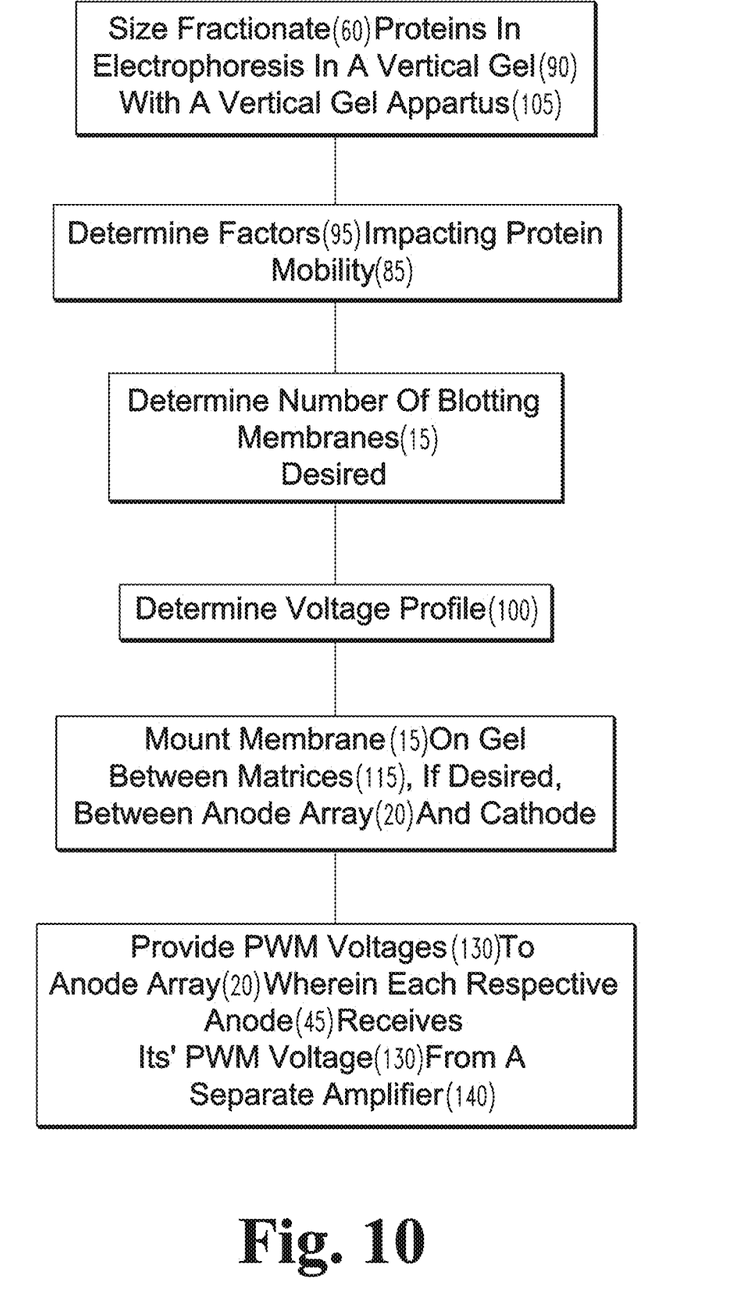
FIG. 10. Diagram of multi-blotting technique incorporating the system of FIG. 2.
Figure 11:
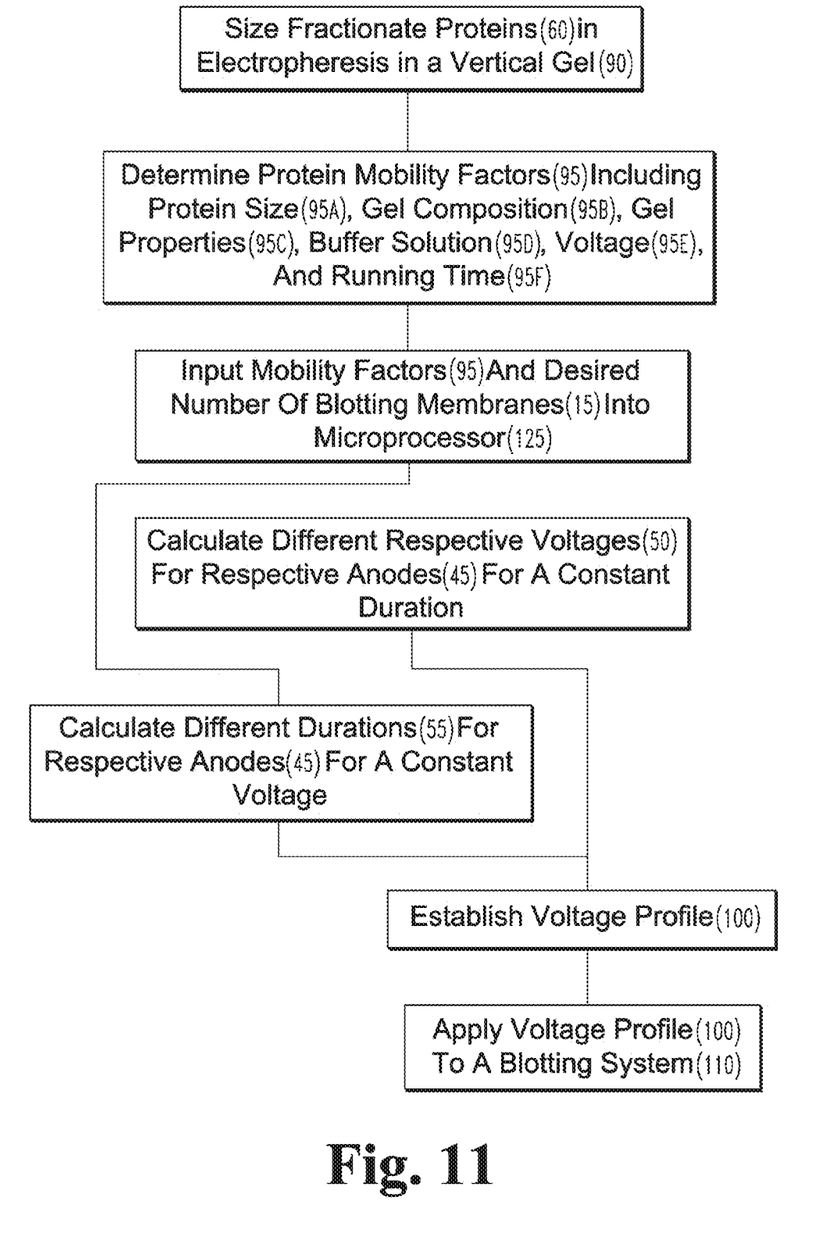
FIG. 11. Diagram of method of determining respective voltages to apply to respective voltages to apply to respective electrodes of system of FIG. 2. when applying technique of FIG. 10.

During blotting, as illustrated in FIGS. 10 and 11, the microcontroller device 125 was configured to request a user to provide the conditions used for protein fractionation with the vertical gel 90 as well as the conditions 95 for protein blotting. The former fractionation conditions 95 included length and the thickness of the gel 95C, electrophoretic voltage 95E, and running time 95F. The latter transferring conditions 95E were the power supply voltage, the number of membranes to be blotted, and buffer solution type 95D used in horizontal blotting and vertical gel 90. The program in the microcontroller 125 calculated the voltage levels needed for each anode 45 and the time required 55 for transferring proteins. Based on the mean and the s.d. values of Gaussian distributions, the blotting time 55 required for each membrane 15 was determined. The program gave a sequence of instructions and guide to a user such as "place the membrane on the device," "start blotting," "wait," "change the membrane," and the like.

The above-described a novel protein multi-blotting device 110 incorporates the multi-anode array 20 and the microcontroller-based voltage-regulating circuits 125. In experimental evaluations, blotting signal intensities were modeled as a cumulative Gaussian distribution function of transferring durations and demonstrated that it was possible to generate 3 blotting membranes 15 from a single gel 65. In the device development phase, an appropriate electrophoretic voltage profile 100 was derived and implemented using the multi-anode plate 20 and the microcontroller based PWM voltage generator 120. The results, using β-actin as an example, supported the notion that the described device 110 was capable of providing superior quality for comparing the level of various proteins, reducing the required amount of samples, time, and cost for protein blotting. In generating a transferring voltage profile 100, it was assumed that protein mobility was proportional to applied voltage and transferring time 55. In order to regulate differential mobility of proteins with varying sizes, the new multi-blotting device 110 generated a well controlled voltage profile 100 in which individual proteins received transferring voltage inversely proportional to its intrinsic mobility. Although this particular design incorporates multi-anodes 20, it is equally possible to build a device using multi-cathodes 21 and a common anode 71.

In predicting transferring time for each of the multiple membranes 15, a protein mobility model using a Gaussian function was constructed. Although average mobility can be characterized by blotting voltage 50 and running time 55, any proteins of interest with same size present a variation in their mobility. Based on experimental results, this variation was approximated by a Gaussian distribution and the amount of proteins transferred to a membrane was predicted from a cumulative Gaussian distribution. By determining the mean and s.d. values, it was possible to divide the transfer process into multiple segments, each of which would receive the equal amount of proteins of interest.

In one embodiment apparatus 110, copper was used as material for the anode 45 and stainless steel for the cathode 70. It was observed that electrical plating occurred and a noticeable amount of cooper was transferred along with proteins to the cathode 70. Other materials such as stainless steel or platinum-titanium alloy may be used to avoid the observed electrical platting during the blotting process.

In predicting and evaluating the capability of the device, commonly used materials and conditions such as 10% SDS gel, a transfer buffer with 70% methanol, and the like were selected. With fine-tuning, the voltage profile 100 and running time 55 for other materials and conditions may be determined. Although the focus of the operation of the described device was on semi-dry blotting, the same principle should apply to dry blotting.

While the novel technology has been illustrated and described in detail in the drawings and foregoing description, the same is to be considered as illustrative and not restrictive in character. It is understood that the embodiments have been shown and described in the foregoing specification in satisfaction of the best mode and enablement requirements. It is understood that one of ordinary skill in the art could readily make a nigh-infinite number of insubstantial changes and modifications to the above-described embodiments and that it would be impractical to attempt to describe all such embodiment variations in the present specification. Accordingly, it is understood that all changes and modifications that come within the spirit of the novel technology are desired to be protected.

What is claimed is:

1. A protein blotting device, comprising:
   a central portion further comprising:
      a membrane; and
      a polyacrylamide gel layer adjacent the membrane;
   first and second matrix layers positioned on opposite sides of the central portion;
   a common cathode plate positioned adjacent the first matrix layer; and
   an anode array positioned adjacent the second matrix layer;
   wherein the first and second matrix layers are in adjacent contact with the central portion.

2. The device of claim 1 wherein the anode array further comprises a plurality of elongated, generally parallel electrodes separated by electrical insulation.

3. The device of claim 2 wherein each respective elongated electrode is provided an independently determined voltage.

4. The device of claim 2 and further comprising:
   a microprocessor;
   a voltage source in electric communication with the anode array and operationally connected to the microprocessor; and
   a ground in electric communication with the cathode plate;
   wherein the microprocessor controls the voltage source to provide each respective electrode with a respective predetermined voltage.

5. The device of claim 4 wherein the microprocessor is programmed to receive data regarding applied voltage, duration of applied voltage, gel dimensions, and protein size fractionation for calibration; wherein the microprocessor is programmed to receive blotting parameters; and wherein the microprocessor is programmed to calculate applied voltage and applied voltage duration to yield for a given set of blotting parameters.

6. A method for simultaneously producing multiple protein blots, comprising:
(a) entering the number 'n' membranes to be blotted into microprocessor memory;
(b) determining calibration constants for a gel batch;
(c) inputting calibration constants into microprocessor memory;
(d) calculating 'n' voltage/time profiles for simultaneous blotting;
(e) treating a gel layer from the gel batch with a protein sample;
(f) placing a membrane onto the gel layer to yield a gel pack;
(g) placing the gel pack between an electrode plate spaced from an array of spaced generally parallel electrodes;
(h) maintaining the electrode plate at a first fixed voltage;
(i) varying the voltage over time to the array of spaced generally parallel electrodes according to a respective voltage/time profile to transfer proteins to a respective membrane to yield a blotted membrane;
(j) removing each respective blotted membrane;
(k) mounting a fresh membrane to the gel layer; and
(l) repeating steps g-j for a total of 'n' cycles.

7. The method of claim 6, wherein the calibration constants are dependent upon various factors including protein sizes, gel buffer solution chemistry, gel buffer solution concentration, electrophoretic voltage, electric field strength, and duration of exposure to electric field.

8. A method for producing multiple protein blots, comprising:
(a) entering the number 'n' membranes to be blotted into microprocessor memory;
(b) determining calibration constants for a gel batch;
(c) inputting calibration constants into microprocessor memory;
(d) calculating 'n' voltage/time profiles for simultaneous blotting;
(e) treating a gel layer from the gel batch with a protein sample;
(f) placing 'n' membranes onto the gel layer to yield a gel pack;
(g) placing the gel pack between an electrode plate spaced from an array of 'n' spaced generally parallel electrodes;
(h) maintaining the electrode plate at a first fixed voltage;
(i) varying the voltage over time to each respective 'n' spaced generally parallel electrodes according to a respective 'n' voltage/time profile to transfer proteins to each respective 'n' membranes to yield blotted membranes; and
(k) removing each respective blotted membrane.

9. A protein blotting device, comprising:
(a) a common electrode plate;
(b) a first matrix layer adjacent to said common electrode plate;
(c) a central layer adjacent to said first matrix layer, further comprising:
a polyacrylamide gel layer; and
a membrane;
(d) a second matrix layer adjacent to said central layer; and
(e) a multiple electrode plate adjacent to said second matrix layer;
wherein said common electrode plate and said multiple electrode plate are oppositely charged.

10. The device of claim 1, wherein the common electrode plate is a cathode and the multiple electrode plate compromises multiple anodes.

11. The device of claim 1, wherein the common electrode plate is an anode and the multiple electrode plate compromises multiple cathodes.

* * * * *